United States Patent [19]

Panetta et al.

[11] 3,985,723
[45] Oct. 12, 1976

[54] TRIFLUOROACETYLATION PROCESS

[75] Inventors: Charles A. Panetta; Travis G. Casanova, both of Oxford, Miss.

[73] Assignee: The University of Mississippi, University, Miss.

[22] Filed: Sept. 7, 1971

[21] Appl. No.: 178,473

[52] U.S. Cl. ............... 260/112.5 R; 260/309.6; 260/313.1; 260/326.14 T; 260/515 A; 260/534 R; 260/534 E; 260/534 G; 260/534 L; 260/534 S; 260/535 R; 260/535 H; 260/557 R; 260/558 R; 260/561 R
[51] Int. Cl.² ............... C07C 103/52; C07C 99/00; C07C 101/00
[58] Field of Search ......... 260/593 R, 557 R, 112.5, 260/309.6, 313.1, 326.14 T, 534 R, 534 E, 534 G, 534 L, 534 S, 535 R, 535 H, 557 R, 558 R, 561 R, 515 A

[56] References Cited
UNITED STATES PATENTS

| 3,446,845 | 5/1969 | Gale | 260/593 R |
| 3,520,929 | 7/1970 | Maravetz et al. | 260/593 R |
| 3,657,341 | 4/1972 | Thorne | 260/557 R |

OTHER PUBLICATIONS

Huntress, E., "Organic Chlorine Compounds", Wiley and Sons, New York (1948), p. 853.
Gilbert, Tetrahedron, 25, 1801 (1969).

*Primary Examiner*—Lewis Gotts
*Assistant Examiner*—Reginald J. Suyat

[57] ABSTRACT

A process for N-trifluoroacetylating an amino compound, such as an amino acid or a peptide, comprising reacting the amino compound with sym-trichlorotrifluoroacetone in a dimethyl sulfoxide solvent under substantially neutral conditions.

10 Claims, No Drawings

TRIFLUOROACETYLATION PROCESS

This invention relates to a novel process for trifluoroacetylating various amino compounds, such as amino acids or peptides.

Trifluoroacetylation is frequently employed in current research on amino acids and peptides, which are the sub-units of the biologically important proteins. The trifluoroacetyl group is quite useful as an alkali-sensitive amino-protecting group for amino acids. It is also used in the preparation of N-trifluoroacetamino acid esters from amino acids derived from natural protein hydrolyzates. These derivatives are volatile and can be analyzed rapidly and quantitatively by gas-liquid chromatography or by fluorine-19 nuclear magnetic resonance spectroscopy.

The trifluoroacetylating reagents most widely used at present are trifluoroacetic acid and trifluoroacetic anhydride. However, these reagents have various disadvantages in that they are strongly acidic materials, have been known to cause peptide bond cleavage during attempts to trifluoroacetylate peptides, and can cause undesired racemization in amino acids.

It has now been found that N-trifluoroacetylation of various amino compounds can be easily effected without the above disadvantages by reacting the amino compound with sym-trichlorotrifluoroacetone in a dimethyl sulfoxide solvent. The reaction can be carried out at room temperature and under mild and substantially neutral conditions. Although the exact mechanism of the reaction has not been determined, the sym-trichlorotrifluoroacetone apparently is cleaved between the carbonyl carbon atom and the trichloromethyl moiety so as to form the N-trifluoroacetylated derivative of the amino compound, in accordance with the following reaction equation:

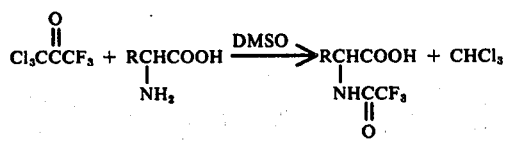

The above reaction is somewhat surprising due to the fact that the reaction of hexafluoroacetone with various amino compounds in dimethyl sulfoxide solvent shows no evidence for the rupture of the carbonyl carbon-trifluoromethyl bond of the ketone. The reaction of hexafluoroacetone with amino acids in dimethyl sulfoxide solvent, for example, has been found to result in the formation of 2,2-bistrifluoromethyl-5-oxazolidones rather than the N-trifluoroacetylamino acids.

The sym-trichlorotrifluoroacetone employed in the process of the present invention may be readily prepared from commercially available chloropentafluoroacetone and aluminum chloride, in accordance with the method described in U.S. Pat. No. 2,807,646, issued Sept. 24, 1957.

The amino compounds which may be N-trifluoroacetylated with sym-trichlorotrifluoroacetone in accordance with the present invention may be any amino compound having at least one hydrogen atom at the nitrogen atom, including, for example, aliphatic, alicyclic, aromatic, araliphatic or heterocyclic amino acids or peptides. Examples of amino acids are, more particularly, L-valine, DL-phenylalanine, L-phenylalanine, L-leucine, L-tyrosine, L-proline and DL-alanine. Examples of peptides include glycylglycine and L-prolylglycine ethyl ester.

The reaction between the amino compound and the sym-trichlorotrifluoroacetone is carried out in a dimethyl sulfoxide solvent under substantially neutral conditions, preferably employing a molar excess of the sym-trichlorotrifluoroacetone. In the preferred practice of the process, the molar ratio of the sym-trichlorotrifluoroacetone to the amino compound in the reaction mixture is approximately 3:1. The reaction may be carried out at room temperature, and at such temperature will be substantially complete in about 24 hours.

The following examples illustrate the practice of the invention:

EXAMPLE 1

A mixture of 7.4 mmol of L-valine, 10 ml of dimethyl sulfoxide and 23 mmol of sym-trichlorotrifluoroacetone was stirred at room temperature for 24 hours in a flask protected from atmospheric moisture. A complete solution was obtained within the first hour. The progress of the reaction was followed by taking samples periodically and submitting them to gas-liquid chromatographic analysis. The reaction mixture was poured into 50 ml of ice water and the resultant mixture was extracted thrice with n-butanol and chromatographed on a column packed with silica gel. N-trifluoroacetylvaline, melting at 88°–89° C., was obtained in a yield of 94 percent.

EXAMPLE 2

A mixture of 7.85 mmol of glycylglycine, 15 ml of dimethyl sulfoxide and 24 mmol of sym-trichlorotrifluoroacetone was stirred at room temperature for 24 hours in a flask protected from atmospheric moisture. The reaction mixture was then poured into 50 ml of ice water and the resultant mixture was extracted thrice with n-butanol and chromatographed on a column packed with silica gel. N-trifluoroacetylglycylglycine, melting at 184.7°–185.0° C., was obtained in a yield of 42.5 percent.

What is claimed is:

1. A process for N-trifluoroacetylating an amino compound having at least one hydrogen atom at the nitrogen atom comprising reacting said amino compound with sym-trichlorotrifluoroacetone.

2. A process according to claim 1, wherein said reaction is carried out in a dimethyl sulfoxide solvent.

3. A process according to claim 1, wherein said reaction is carried out under substantially neutral conditions.

4. A process according to claim 1, wherein said reaction is carried out at room temperature.

5. A process according to claim 1, wherein the molar ratio of sym-trichlorotrifluoroacetone to amino compound present in the reaction mixture is approximately 3:1.

6. A process according to claim 1, wherein said amino compound is an amino acid.

7. A process according to claim 1 wherein said amino compound is a peptide.

8. A process for N-trifluoroacetylating an amino compound having at least one hydrogen atom at the nitrogen atom comprising reacting said amino compound with sym-trichlorotrifluoroacetone in a dimethyl sulfoxide solvent at room temperature under substantially neutral conditions.

9. A process according to claim 8 wherein said amino compound is an amino acid.

10. A process according to claim 8 wherein said amino compound is a peptide.

* * * * *